United States Patent [19]

Dorman et al.

[11] Patent Number: 5,073,094

[45] Date of Patent: Dec. 17, 1991

[54] ZERO NET EXTERNAL DISPLACEMENT IMPLANTABLE PUMP AND DRIVER

[75] Inventors: Frank D. Dorman; Bruce D. Wigness, both of Minneapolis, Minn.

[73] Assignee: Regents of the University of Minnesota, Minneapolis, Minn.

[21] Appl. No.: 121,649

[22] Filed: Nov. 17, 1987

[51] Int. Cl.[5] ...................... F04B 43/00; A61M 37/00; A61M 5/00; F16J 3/00

[52] U.S. Cl. ..................................... 417/412; 417/473; 604/131; 604/9; 92/47

[58] Field of Search ............... 417/412, 413, 472, 473, 417/481, 482; 92/34; 623/3; 604/131, 134, 151, 153, 891.1

[56] References Cited

U.S. PATENT DOCUMENTS

| 5,770 | 9/1848 | Deshon et al. | 417/473 |
| 20,045 | 4/1858 | Cumming | 417/473 X |
| 2,334,525 | 11/1943 | Zadig | 417/473 |
| 3,330,902 | 7/1967 | Nakazawa et al. | 92/47 |
| 3,809,087 | 5/1974 | Lewis, Jr. | 604/134 |
| 4,058,857 | 11/1977 | Runge et al. | 417/412 X |
| 4,265,241 | 5/1981 | Portner et al. | 604/131 |
| 4,335,835 | 6/1982 | Beigler et al. | 604/131 |
| 4,657,530 | 4/1987 | Buchwald et al. | 604/9 |
| 4,657,536 | 4/1987 | Dorman | 604/9 X |

Primary Examiner—Richard A. Bertsch
Attorney, Agent, or Firm—Burd, Bartz & Gutenkauf

[57] ABSTRACT

A zero net external displacement implantable pump for the transfer of accumulated body fluids, such as transfer of ascites fluid from the peritoneum to the vasculative system. The pump includes a pair of bellows type displacement chambers which are alternately compressed and expanded by action of a pivoted rocker member. The fluid to be transferred is drawn into the chambers on the expansion strokes and expelled on the compression strokes. The rocker member may be operated manually or power driven. Single action and double action pumps are disclosed.

17 Claims, 3 Drawing Sheets

ZERO NET EXTERNAL DISPLACEMENT IMPLANTABLE PUMP AND DRIVER

BACKGROUND OF THE INVENTION

1. Field of the Invention

This invention relates to a zero net external displacement implantable pump and driver intended primarily for use in connection with an implantable anti-reflux fluid displacement peritoneovenous shunt used to transfer an unwanted accumulation of body fluids from a body cavity to a site where it can be processed by the body. The primary use for the shunt is in the treatment of patients with ascites by the displacement of accumulated peritoneal cavity fluid into the systemic venous circulation.

This application is related to Buchwald et al U.S. Pat. No. 4,657,530, issued Apr. 14, 1987, entitled Compression Pump-Catheter and directed to a manually operable ascites shunt. The device of the aforesaid patent is a peritoneovenous shunt in which ascites fluid is transferred from the peritoneum to the vasculature via a manually operated compression pump. That device is not a viable alternative for certain patients who require peritoneovenous shunting but for a variety of reasons are unable to perform the pumping mechanics.

To operate such a manually compressible pump implanted within the body by compression of the body surface over the pump, there must be some net displacement of volume. This displacement can take place within the pump in which case there must be adequate internal pressure resisting the applied pressure to return the pump to its original state for the next stroke. This internal pressure, supplied by spring action, must be great enough to expand the overlaying tissue to its original position as well as provide all the negative pressure for the pump intake stroke. During the compression stroke of the pump, one must therefore provide the summation of the output back pressure and the spring compression force for the inlet suction as well as some excess pressure to insure that the tissue deformation force is overcome. The pump according to the present invention reduces the force needed for operation by using a two stroke dual action pump that has zero net external displacement.

2. The Prior Art

No pertinent prior art is known.

SUMMARY OF THE INVENTION

The pump of the present invention includes a pair of bellows type displacement chambers. A rocker action allows the compression stroke of one chamber to cause an expension stroke of the other chamber by internal mechanical coupling. Thus no spring return force is needed. The operator alternately compresses the two sides of the pump in a rocking action. Each stroke needs only to overcome the valve opening pressure, the fluid flow resistance and any net pressure difference between the peritoneal cavity and the blood stream. If there is resistance to movement by the overlaying tissue, this is overcome by direct compression force and does not need any preset spring force. Although there is zero net displacement of the tissue, the area overlaying the pump must move to allow mechanical energy to be transferred to do the pumping work when the pump is used alone in the manually operated mode.

Broadly stated, the pump comprises a pair of bellows chambers in side-by-side relation. An inlet to and a discharge outlet from each of the chambers is provided. A check valve is provided in each of the inlet and outlet flow lines to regulate one way flow through the pump. A rocker plate is provided which overlies both of the pump chambers and is pivotable on an axis between the chambers. Rocking of the plate alternately compresses each of the chambers to draw fluid into one chamber and discharge fluid from the other. The pump may be manually or mechanically operated.

The pump may be single or double acting. That is, in a single action pump fluid is drawn first into one chamber on the first stroke of the rocking plate, transferred to the other chamber on the next stroke, and then discharged to the bloodstream of the patient on the following stroke as the first chamber is being refilled. In a double acting pump, as one chamber is being filled the contents of the other chamber are being discharged to the bloodstream. On the next stroke the contents of the first chamber are discharged directly to the bloodstream as the other chamber is being refilled directly from the peritoneal fluid collector.

BRIEF DESCRIPTION OF THE DRAWINGS

The invention is illustrated in the accompanying drawings in which corresponding parts are identified by the same numerals and in which.

DETAILED DESCRIPTION OF THE PREFERRED EMBODIMENT

Figure 1:
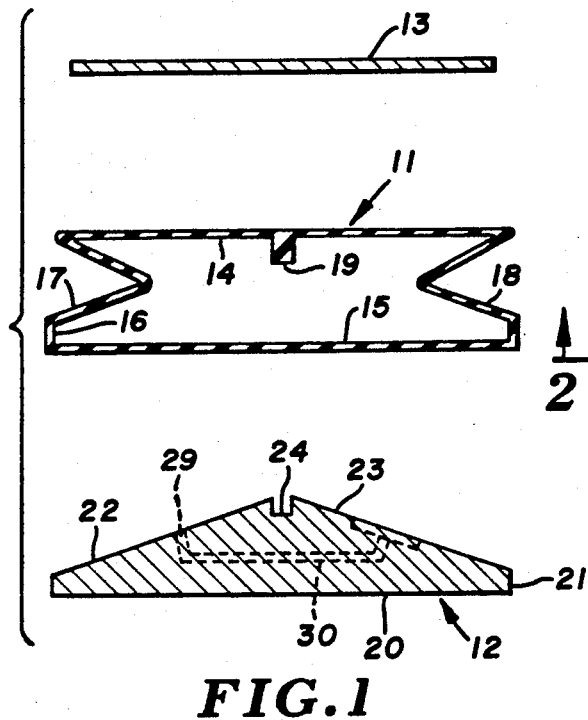
FIG. 1 is an exploded view in section showing the essential components of the pump according to the present invention.
Figure 3:
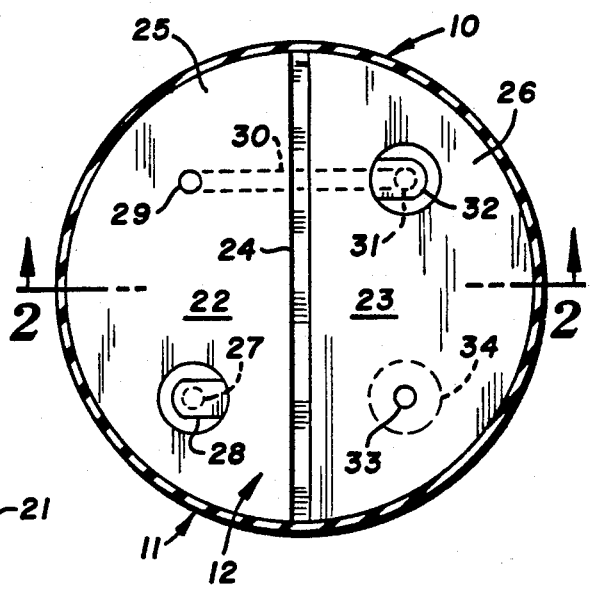
FIG. 3 is a plan view of the assembled pump, partially in section on the line 3—3 of FIG. 2, and in the direction of the arrows.
Figure 2:
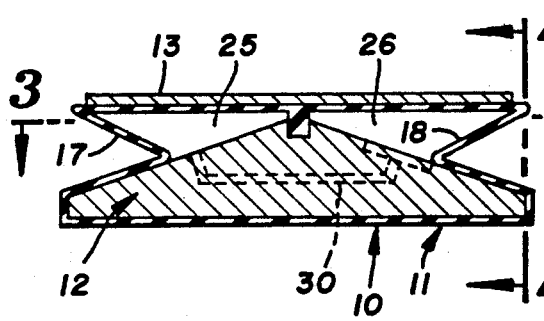
FIG. 2 is an elevation in section of the assembled pump components.
Figure 4:
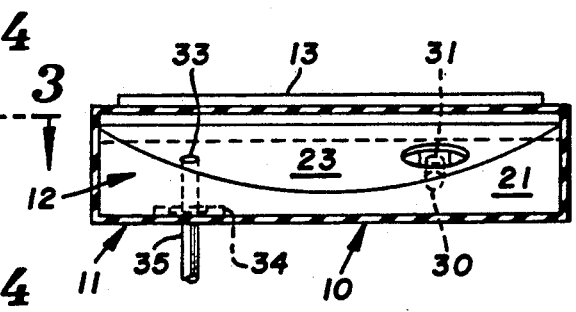
FIG. 4 is a side elevation in partial section on the line 4—4 of FIG. 2, and in the direction of the arrows.

Referring now to the drawings, and particularly to FIGS. 1 to 6, there is shown one form of single action zero net external displacement implantable pump according to the present invention. The pump, indicated generally at 10, is comprised of three basic components, an elastomeric bladder 11, a solid generally rigid base member 10, and a rocker plate 13. The pump 10 is of overall flat generally cylindrical configuration of a size adapted to be implanted under the skin of a living animal, including humans. Bladder 11 may be formed, for example, by dipping a form of proper configuration into a suspension of natural or synthetic rubber or rubber-like latex. A preferred material is medical grade silicone rubber.

Bladder 11 includes circular top and bottom walls 14 and 15, respectively, and annular side wall 16. At least one bellows pleat 17 and 18 is formed in the bladder side wall on opposite sides thereof. A tongue 19 depends from the inside top wall 14 of the bladder along a diameter of the top wall spaced equidistant from the bellows pleats 17 and 18.

Reference herein to "top" and "bottom" and the like is in relation to the elements as shown in the drawings. This is independent of the positioning of those elements in the assembled pump when implanted for use in a living being.

Base member 12 is generally in the form of a flat solid cylinder having a bottom wall 20, annular side wall 21, and a pair of top faces 22 and 23 tapering downwardly from a diametric center line at the top of the base member. A groove 24 is formed in the top surface of the base member along the center line separating the tapered faces 22 and 23.

Bladder 11 and base member 12 are of such a size and shape that when assembled tongue 19 fits into and engages groove 24 in close generally fluid-tight engagement. Bladder bottom wall 15 and base member bottom wall 20 and bladder annular side wall 16 and base member side wall 21 are also in close generally fluid-tight engagement with one another.

Figure 5:
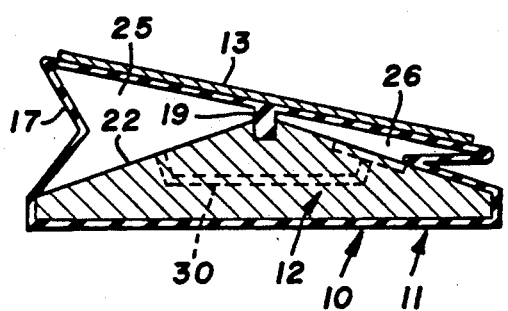
FIG. 5 is an elevation in section of the assembled pump in one pumping mode.
Figure 6:
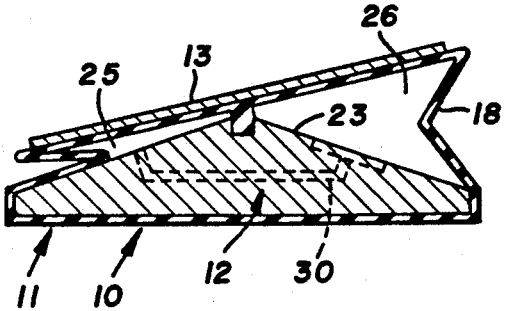
FIG. 6 is a similar section showing the pump in the other pumping mode.

A first fluid chamber 25 is formed in the space between base member tapered top face 22, bellows pleat 17 and the adjacent half of the bladder top wall. A second fluid chamber 26 is similarly formed between the base member face 23, bellows pleat 18 and the other half of the bladder top wall. As best seen by comparison of FIGS. 5 and 6, when rocker plate 13 is pivoted on an axis along the center line overlying groove 24 and tongue 19, the volumes of chambers 25 and 26 may be alternately enlarged and made smaller. When chamber 25 is expanded, as shown in FIG. 5, fluid may be drawn into that chamber through appropriate ports and connections to a source of fluid to be pumped. At the same time, any fluid in chamber 26 is expelled. When the rocker plate is pivoted in the opposite direction, as shown in FIG. 6, fluid in chamber 25 is drawn into chamber 26 as it is expelled from chamber 25.

Various configurations of ports, passages and external connections are possible dependent upon the desired mode of operation of the pump. In the embodiment shown in FIGS. 1 through 6, there is an inlet port 27 to chamber 25 which is adapted to be connected through means (not shown) to a source of fluid to be transferred, such as an ascites fluid collector. Port 27 is closed by a flexible flap member 28 functioning as a check valve to regulate one way flow through the pump chamber. An outlet port 29 from chamber 25 connects through passage 30 to inlet port 31 to chamber 26. Port 31 is closed by flexible flap 32 forming a further check valve. Discharge port 33 from chamber 26 connects through a further flap valve 34 to a flow line 35 for discharge of the fluid to the bloodstream, for example.

Figure 7:
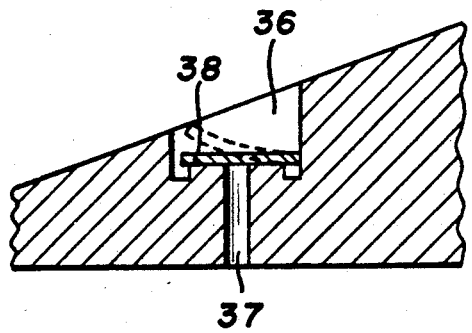
FIG. 7 is a sectional view, on an enlarged scale of one form of flap check valve for the inlet to the pump chambers.
Figure 8:
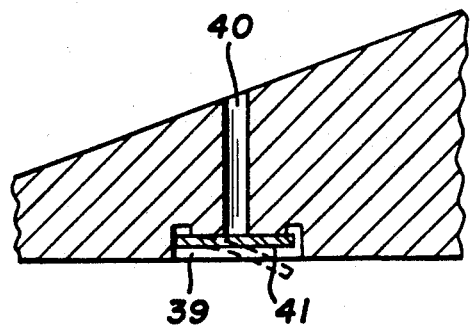
FIG. 8 is a similar sectional view of a flap check valve for the outlet from the pump chambers.

FIG. 7 shows a typical inlet port flap check valve 36 in greater detail. The port at the end of passage 37 is closed by a flexible flap 38, preferably recessed below the surface of the base member. Similarly, FIG. 8 shows a typical discharge port flap check valve 39 in greater detail. The discharge port at the end of passage 40 is closed by flexible flap 41 which is preferably recessed within the base member.

Figure 9:
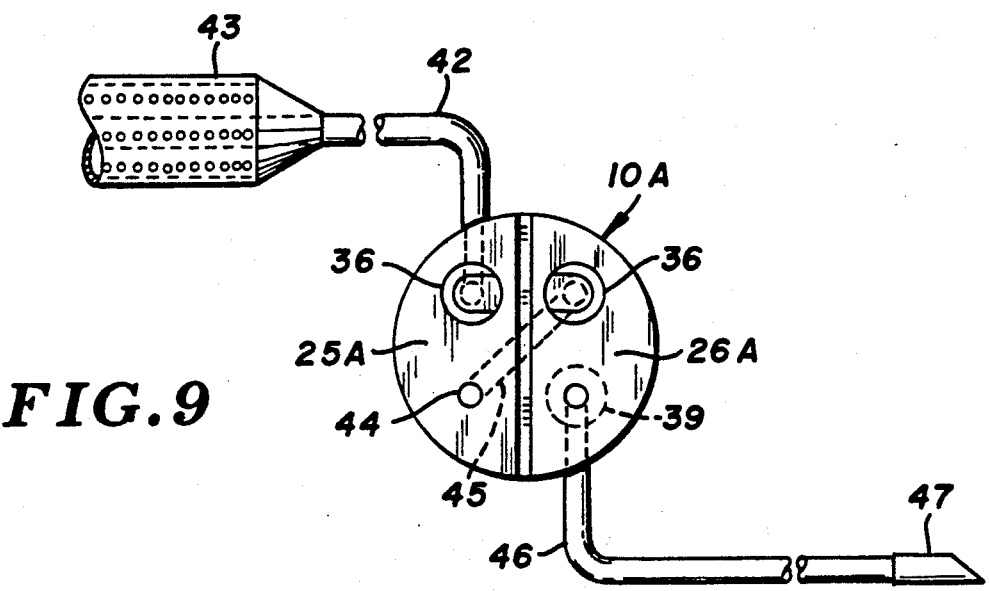
FIG. 9 is a schematic representation of a peritoneovenous shunt system including a single action pump.

FIG. 9 illustrates schematically the use of a single action pump 10A of slightly different configuration in a peritoneovenous shunt system and the manner in which flow line connections are made. The pump 10A is connected through a flow line in the form of flexible tubing 42 to an ascites fluid collector 43 of the type disclosed in Buchwald et al U.S. Pat. No. 4,657,530. On the expansion stroke of chamber 25, a fluid from the collector 43 and tubing 44 enters the chamber through check valve 36. On the compression stroke of chamber 25A, that fluid is forced through discharge port 34 and passage 45 and on the concurrent expansion stroke of chamber 26A is drawn through check valve 36 into the chamber. On the compression stroke of chamber 26A that fluid is forced through the discharge port and check valve 39 into catheter 46 for transfer to a body site, such as the venous system, where the fluid may be processed by the body. Preferably the catheter 46 is fitted with a check valve catheter tip 47 of the type disclosed in Dorman U.S. Pat. No. 4,657,536.

Figure 10:
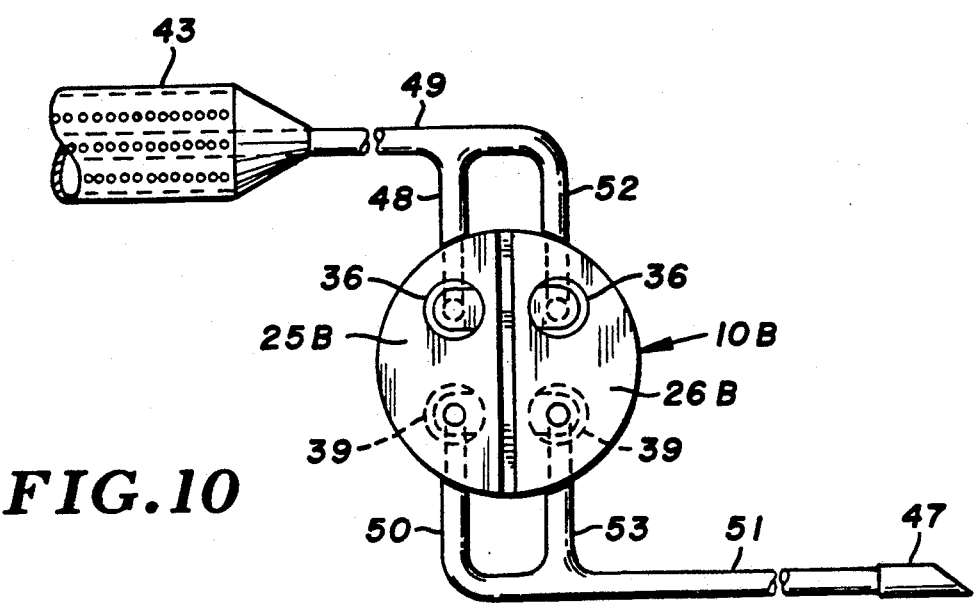
FIG. 10 is a similar representation of a system including a double action pump.
Figure 11:
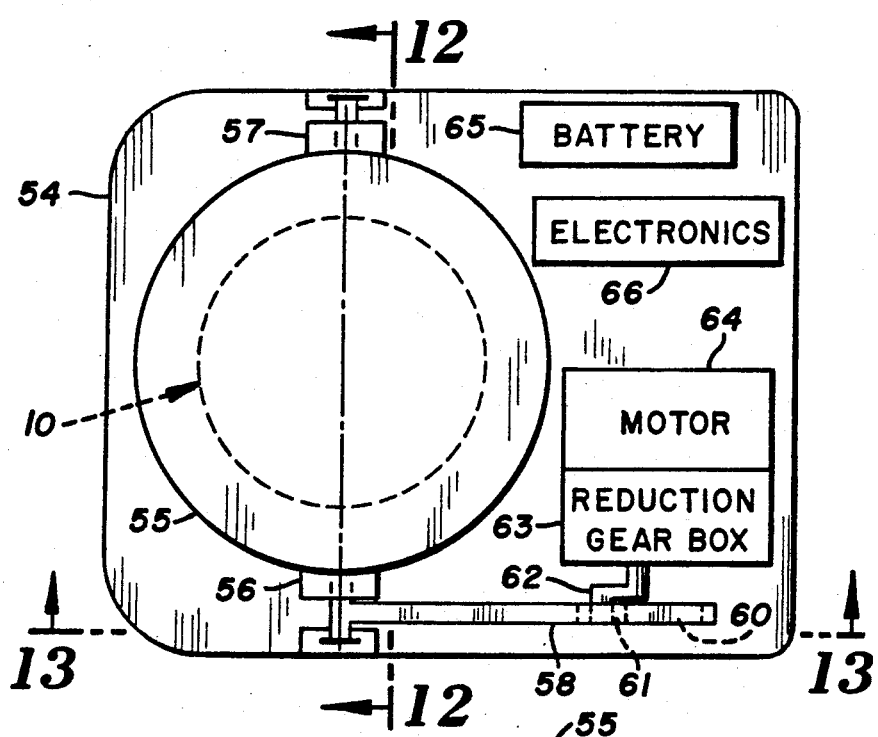
FIG. 11 is a schematic plan view of one form of driver for the pump of the present invention.
Figure 12:
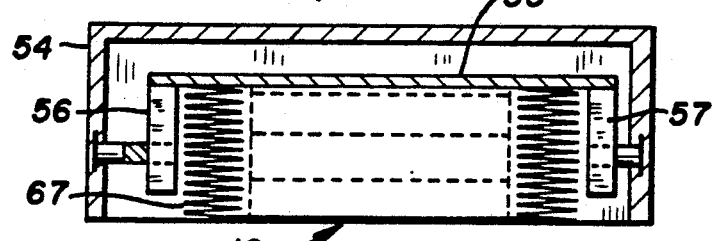
FIG. 12 is a section on the line 12—12 of FIG. 11 and in the direction of the arrows.

FIG. 10 illustrates schematically a similar peritoneovenous shunt system utilizing a double action pump 10B according to the present invention. Twice as much fluid is pumped by each stroke in the double action configuration. Pump chamber 25B is connected through flow lines in the form of flexible tubing 48 and 49 to collector 43. Chamber 25B is also connected through a flow line in the form of tubing 50 to catheter 51 for discharge of the fluid through tip 47. Chamber 26B is also connected to collector 43 through flow lines in the form of tubing 52 and 49 and to the catheter 51 through tubing 53.

On the expansion stroke of chamber 25B fluid is drawn into that chamber through check valve 36. Simultaneously during the compression stroke of chamber 26B, the fluid collected in that chamber is discharged through check valve 39 and tubing 53 to catheter 51 for distribution into the bloodstream. Fluid is drawn into chamber 26B during the compression stroke of chamber 25B, and simultaneously the fluid in that chamber is discharged from the pump.

Referring now to FIGS. 11 through 14, there is shown one form of automated power drive for the pump according to the present invention. The pump 10 is enclosed in a cavity within housing 54. A rocker plate 55 is provided with a pair of depending leg members 56 and 57 spaced at opposite ends of the diametric center line which overlies the diametric center line of the pump. The rocker plate is journaled for limited pivotal rocking movement. When the pump is in place in the cavity the axis of the pump is aligned with the axis defined by the bearing of the rocker plate. A rigid link in the form of arm 58 is fixedly attached to the rocker leg member 56 for concurrent movement. The opposite end of arm 58 is provided with a cam slot 60 in which a roller cam 61 reciprocates. Roller cam 61 is journaled for rotation relative to the end of a crank arm 62 driven through a gear box 63 of appropriate reduction by motor 64.

Motor 64 is powered by battery 65. Operation of the motor 64 by battery 65 is actuated through electronic control means 66 dependent upon the needs of the patient in whom the pump is implanted. The electronic control may be as simple as a pressure-sensitive on-off switch, or the motor may be operated in a preprogrammed timed sequence, or the like. Battery 65 should be rechargeable by means of a power telemetry system commonly used for implanted electronic devices.

Preferably the electronically driven pump includes a metal bellows 67 comprised of a stack of a plurality of concentric flat annular rings secured together alternately at their inner and outer peripheries. The topmost ring is secured to the rocker plate 55. The pump 10 may be hermetically sealed within the bellows, flow lines to and from the pump being through connections, not shown, in the bottom plate of the bellows.

Figure 13:
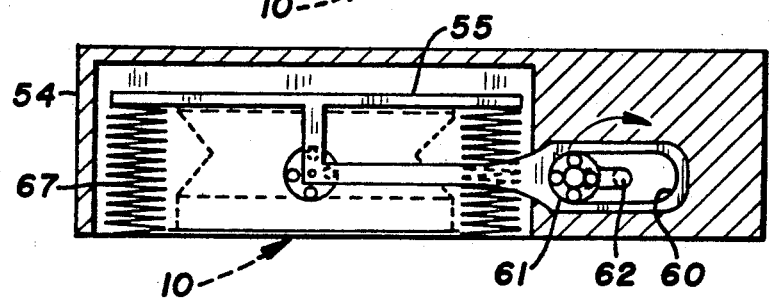
FIG. 13 is a section on the line 13—13 of FIG. 11 and in the direction of the arrows.
Figure 14:
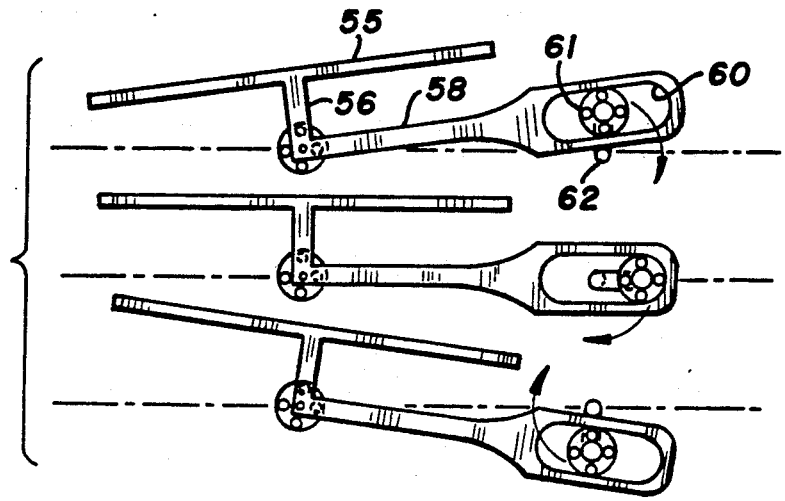
FIG. 14 shows the several different operating positions of the driver mechanism.

As seen in FIGS. 13 and 14, operation of motor 64 causes rotation of crank arm 62. Rotation of cam roller 61 within slot 60 induces rocking motion in arm 58 which causes limited pivotal movement of rocker plate 55 to provide the same rocker action as manual operation.

The drive unit is a separate sealed unit that supplies only mechanical power to the pump unit. No body fluids enter the drive housing where sensitive electronic components may be located. Any diffusion of fluids through the pump components held in the driver housing cavity are returned to the body and cannot enter the drive unit.

All of the implantable pump structure which is in contact with body fluids or tissue is composed of inert stable non-toxic biocompatible materials. A preferred material for components such as tubular flow lines is medical grade silicone rubber tubing. Connections may be sealed with medical grade Silastic adhesive. The motor driven pump housing may be sealed and coated with silicone rubber, or polytetrafluoroethylene (Teflon), or similar material compatible with body fluids and well known for the coating of devices to be implanted within the body.

Dimensions are not critical and the peritoneovenous shunt system is sized to meet particular needs. At the same time, the components should be as small as possible, consistent with the needs of the patient, to facilitate implantation.

It is apparent that many modifications and variations of this invention as hereinbefore set forth may be made without departing from the spirit and scope thereof. The specific embodiments described are given by way of example only and the invention is limited only by the terms of the appended claims.

We claim:

1. An implantable anti-reflux fluid displacement compression pump-catheter system which comprises:
A) a body fluid collecting device;
B) a zero net external displacement pump including:
   1) a pair of bellows chambers in adjacent side-by-side relation, each of said chambers having one generally flat wall which is substantially coplanar with the corresponding wall of the adjacent chamber;
   2) an inlet to and a discharge outlet from each of said chambers;
   3) a check valve in each of the inlet and outlet flow lines regulating one way flow through the pump; and
   4) a single rocker plate overlying the coplanar walls of both of said chambers and pivotable on an axis between said chambers to permit alternate compression and expansion of each of the chambers, said pump being enclosed in an implantable housing including:
      a) a cavity adapted to receive said pump;
      b) pivot means journaling said rocker plate for limiting rocking motion within said cavity;
      c) crank arm and link drive means operatively connected to said rocker plate; and
      d) battery driven motor means for rotating said crank arm;
C) a tubular connection between said fluid collecting device and said pump; and
D) a catheter connected to said pump for distribution of collected body fluid to a selected body site.

2. A system according to claim 1 wherein said pump bellows chambers are collapsible elastomeric pouches.

3. A system according to claim 1 wherein the pump is a single action pump, the chambers of the pump are interconnected by a flow passage, and the discharge outlet from the first chamber and the inlet to the other chamber are connected to said passage.

4. A system according to claim 1 wherein the pump is a double action pump, the chambers of the pump are independent one from the other, the inlets to both chambers are adapted for connection to a single source of fluid to be pumped and the discharge outlets of both chambers are adapted for connection to a single discharge flow line chamber.

5. A system according to claim 1 wherein a cylindrical bellows composed of a plurality of interconnected circular rings is disposed within said cavity and said pump is disposed within said bellows.

6. An implantable anti-reflux fluid displacement compression pump-catheter system which comprises:
A) a body fluid collecting device;
B) a single action zero net external displacement pump including:
   1) a pair of bellows chambers in adjacent side-by-side relation, each of said chambers having one generally flat wall which is substantially coplanar with the corresponding wall of the adjacent chamber;
   2) an inlet to the first of said chambers and a discharge outlet from the other of said chambers;
   3) a passage connecting said chambers;
   4) a check valve in each of the inlet and outlet and connecting passage flow lines regulating one way flow through the pump; and
   5) a single rocker plate overlying the coplanar walls of both of said chambers and pivotable on an axis between said chambers to permit alternate compression and expansion of each of the chambers; said pump being enclosed in an implantable housing including:
      a) a cavity adapted to receive said pump;
      b) pivot means journaling said rocker plate for limited rocking motion within said cavity;
      c) crank arm and link drive means operatively connected to said rocker plate; and
      d) battery driven motor means for rotating said crank arm;
C) a tubular connection between said fluid collecting device and said inlet to the first pump chamber; and
D) a catheter connected to the discharge outlet of said other pump chamber for distribution of collected body fluid to a selected body site.

7. A system according to claim 6 wherein said pump bellows chambers are collapsible elastomeric pouches.

8. A system according to claim 6 wherein a cylindrical bellows composed of a plurality of interconnected circular rings is disposed within said cavity and said pump is disposed within said bellows.

9. An implantable anti-reflux fluid displacement compression pump-catheter system which comprises:
A) a body fluid collecting device;
B) a double action zero net external displacement pump including:
1) a pair of bellows chambers in adjacent side-by-side relation, each of said chambers having one generally flat wall which is substantially coplanar with the corresponding wall of the adjacent chamber, and said chambers being independent one from the other;
2) separate inlets to each of said chambers, said inlets being adapted for connection to a single source of fluid to be pumped;
3) separate discharge outlets from each of said chambers, said outlets being adapted for connection to a single discharge flow line;
4) a check valve in each of the inlet and outlet flow lines regulating one way flow through each of the chambers; and
5) a single rocker plate overlying the coplanar walls of both of said chambers and pivoted on an axis between said chambers to permit alternate compression and expansion of each of the chambers; said pump being enclosed in an implantable housing including:
a) a cavity adapted to receive said pump;
b) pivot means journaling said rocker plate for limited rocking motion within said cavity;
c) crank arm and link drive means operatively connected to said rocker plate; and
d) battery driven motor means for rotating said crank arm;
C) a tubular connection between said fluid collecting device and each of said inlets; and
D) a catheter connected to said discharge flow line for distribution of body fluid to a body site.

10. A system according to claim 9 wherein said bellows chambers are collapsible elastomeric pouches.

11. A system according to claim 9 wherein a cylindrical bellows comprised of a plurality of interconnected circular rings is disposed within said cavity and said pump is disposed within said bellows.

12. A zero net external displacement pump for implantation within a living animal body for use in an anti-reflux fluid displacement compression pump-catheter system, said pump comprising:
A) a flat generally cylindrical base member having top faces tapering downwardly from a diametric center line;
B) a groove along said center line;
C) a flat generally cylindrical elastomeric bladder surrounding said base member in close generally fluid tight engagement with the bottom and side walls of the base member and defining a pair of bellows chambers in adjacent side-by-side relation;
D) an internal diametric tongue depending from the top wall of said bladder in generally fluid tight engagement with the diametric groove in the base member;
E) bellows pleats in the sides of said bladder;
F) a fluid inlet passage to and discharge outlet passage from each of said chambers formed within said base member;
G) a check valve in each of the inlet and outlet passages regulating one way flow through the pump; and
H) a rocker plate overlying both of said bellows chambers and pivotable on an axis between said chambers to permit alternate compression and expansion of each of the chambers.

13. A pump according to claim 12 wherein said elastomeric bladder is formed from silicone rubber.

14. A single action zero net external displacement pump for implantation within a living animal body for use in an anti-reflux fluid displacement compression pump-catheter system, said pump comprising:
A) a flat generally cylindrical base member having top faces tapering downwardly from a diametric center line;
B) a groove along said center line;
C) a flat generally cylindrical elastomeric bladder surrounding said base member in close generally fluid tight engagement with the bottom and side walls of the base member and defining a pair of bellows chambers in adjacent side-by-side relation;
D) an internal diametric tongue depending from the top wall of said bladder in generally fluid tight engagement with the diametric groove in the base member;
E) bellows pleats in the side of said bladder;
F) a fluid inlet passage to the first of said chambers and a discharge outlet passage from the other of said chambers, said passages formed within said base member;
G) a passage within said base member connecting said chambers;
H) a check valve in each of the inlet and outlet and connecting passage flow lines regulating one way flow through the pump; and
I) a rocker plate overlying both of said bellows chambers and pivotable on an axis between said chambers to permit alternate compression and expansion of each of the chambers.

15. A pump according to claim 14 wherein said elastomeric bladder is formed from silicone rubber.

16. A double action zero net external displacement pump for implantation within a living animal body for use in an anti-reflux fluid displacement compression pump-catheter system, said pump comprising:
A) a flat generally cylindrical base member having top faces tapering downwardly from a diametric center line;
B) a groove along said center line;
C) a flat generally cylindrical elastomeric bladder surrounding said base member in close generally fluid tight engagement with the bottom and side walls of the base member and defining a pair of bellows chambers in adjacent side-by-side relation, said chambers being independent one from the other;
D) an internal diametric tongue depending from the top wall of said bladder in generally fluid tight engagement with the diametric groove in the base member;
E) bellows pleats in the sides of said bladder;
F) separate fluid inlet passages to each of said bellows chambers, said inlet passages being adapted for connection to a single source of fluid to be pumped;
G) separate fluid discharge outlet passages from each of said chambers, said outlet passages being adapted for connection to a single discharge flow line;
H) a check valve in each of the inlet and outlet passage flow lines regulating one way flow through each of the chambers; and
I) a rocker plate overlying both of said bellows chambers and pivoted on an axis between said chambers to permit alternate compression and expansion of each of the chambers.

17. A pump according to claim 16 wherein said elastomeric bladder is formed from silicone rubber.

* * * * *

UNITED STATES PATENT AND TRADEMARK OFFICE
CERTIFICATE OF CORRECTION

PATENT NO. : 5,073,094

DATED : December 17, 1991

INVENTOR(S) : FRANK D. DORMAN et al

It is certified that error appears in the above-identified patent and that said Letters Patent is hereby corrected as shown below:

Column 1, line 3  insert the follwing:

---This invention was made with government support under POSCH grant 5R01-HL 15265 awarded by the National Institutes of Health.  The government has certain rights in the invention.---

Signed and Sealed this

Twenty-eighth Day of November 1995

Attest:

BRUCE LEHMAN

Attesting Officer

Commissioner of Patents and Trademarks